United States Patent [19]
Eggleton

[11] 3,955,561
[45] May 11, 1976

[54] CARDIOSCAN PROBE

[75] Inventor: Reginald C. Eggleton, Indianapolis, Ind.

[73] Assignee: Indianapolis Center for Advanced Research, Inc., Indianapolis, Ind.

[22] Filed: Sept. 16, 1974

[21] Appl. No.: 506,565

[52] U.S. Cl. .......................... 128/2.05 Z; 73/67.8 S; 128/24 A
[51] Int. Cl.² .......................................... A61B 10/00
[58] Field of Search ............ 128/2 V, 2.05 Z, 24 A; 73/67.5 R, 67.7, 67.8 S; 310/9.1

[56] References Cited
UNITED STATES PATENTS

| | | | |
|---|---|---|---|
| 3,470,868 | 10/1969 | Krause et al. | 73/67.8 S |
| 3,550,075 | 12/1970 | Hilche et al. | 73/67.5 R |
| 3,584,504 | 6/1971 | Proctor | 73/67.8 S |
| 3,763,463 | 10/1973 | Muir | 73/67.7 |
| 3,817,089 | 6/1974 | Eggleton et al. | 73/67.8 S |

*Primary Examiner*—William E. Kamm
*Attorney, Agent, or Firm*—Woodard, Weikart, Emhardt & Naughton

[57] ABSTRACT

Ultrasonic probe apparatus for real time B-mode sector scan examination of a cross section of a structure such as the human heart. A transducer is pivotally mounted near an end of an elongated housing, and linkage means are provided in the housing for oscillating the transducer about an axis whose plane is approximately perpendicular to the longest dimension of the housing. Means are provided for causing the transducer to produce ultrasonic pulses which are reflected by interfaces of the object under examination, and the echoes from these interfaces are returned through the transducer to a B-mode display system. A B-mode sector sweep circuit is provided to produce a B-mode display of the echo pattern received from the structure being observed.

9 Claims, 6 Drawing Figures

CARDIOSCAN PROBE

The invention is in the field of B-mode ultrasonic probe systems.

The present disclosure concerns an ultrasonic system for examination of interior portions of various structures. In particular, the disclosure pertains to a medical ultrasonic system for examination of the human heart and particularly to provide real time B-mode examination of a cross section of the heart. Presently, M-mode echo cardiography is extensively used for diagnosis of heart disease in most of the major medical centers of the world. The system described herein is designed to be compatible with existing M-mode echo cardiography and utilizes the same type of transducers now commonly in use with the M-mode technique, as well as the pulsers and amplifiers, power supplies and associated components normally included in the M-mode echocardiographic systems.

B-mode systems for viewing internal structures of the human body have been disclosed in U.S. Pat. Nos. 3,403,671, 3,480,002 and 3,605,724, all to Flaherty; No. 3,547,101 to Rosauer; and Nos. 3,779,234 and 3,817,089 to Eggleton et al. These patents have shown ultrasonic B-mode techniques wherein a transducer is rotated or oscillated about an axis parallel to the primary axis of the probe. This orientation limits the freedom of movement and angle of approach to a structure, such as the human heart, which would be available from a transducer oscillating about an axis in a plane perpendicular to the main axis of the probe. In this latter arrangement, the transducer is located at an end of the probe and the operator can choose the direction of approach to the structure to be viewed freely.

The patents cited above further disclose sweep display systems dependent upon either a sine-cosine potentiometer or rotor coils in the probe to develop signals having amplitudes which are sine and cosine functions of the angular position of the shaft on which the transducer rotates or oscillates. So far as applicant is aware, the sweep circuitry disclosed herein has not been utilized in the past for B-mode display.

The B-mode system of the present application is designed as a rectrofit package compatible with existing M-mode systems. In order to accomplish an adequate diagnostic procedure, a physician must be free to direct the acoustic beam toward the structures of interest in the heart, and at the proper angle of approach, in order to make use of specular reflections from the surfaces of the structures. The determination of the angles of approach is done using a free-hand searching technique which involves optimizing the field of view provided by the B-mode scanning system. The physician or technologist operating the device requires a freedom of motion of the transducer, which can only be achieved by a light-weight hand-held scanning unit in which the axis of rotation of the transducer lies in a plane perpendicular to the axis of the probe housing. With the transducer thus mounted for oscillatory sector scan motion at the end of the probe housing, the assembly can be directed at essentially any angle required for optimum viewing of the patient's heart or other internal structure.

Examinations by the physician or technologist in a busy medical center may be conducted over extended periods of time, and therefore the scanning unit must be sufficiently light weight that it does not become tiresome for the Examiner nor uncomfortable to the patient. In order to meaningfully examine dynamic aspects of the heart, it is also necessary to optimize the data acquisition rate. This rate is essentially limited by the speed of sound in tissue, approximately 1.5 millimeters per microsecond. The pulse emitted by the transducer must propagate through the tissue and reflect from targets and return to the transducer before the next pulse is emitted, and there must be a choice of perameters which optimize the data acquisition rate for selected examination. Whereas it has been customary to limit the pulse repetition frequency (PRF) of ultrasonic systems to the range of 250 pulses per second to 1,000 pulses per second, the present system provides a selectable PRF of, for example, 5,000 cycles per second. In order to accomplish this, it is necessary to utilize special sweep circuitry with extremely fast fly back capabilities. With a 5,000 PRF, it is possible to examine tissue in the area of the human heart to a depth of 15 centimeters, and obtain 50 frames per second with 100 lines per frame. By limiting the sector to 30°, it is possible to achieve line density of 3.3 lines per degree on an oscilloscope screen.

Flicker fusion occurs for the human visual system at about 40 frames per second, depending upon the intensity, color of the light, and the mark space ratio of the light flashes. To achieve detail concerning valvular motion of the heart, it is necessary to utilize the highest possible scan rate consistent with the depth of examination and the acoustic perameters. Thus, it is desirable that the physician be provided with a means of controlling the scanning rate. Frame rates in the order from 5 to 20 frames per second are not particularly useful, and may be disquieting to the physician and patient because the normal alpha rhythm of human beings is in this frequency range, and looking at a flicker of this frequency may drive the alpha waves within the brain and, in some instances, trigger a convulsive reaction if the person viewing the screen is subjected to prolonged periods of this excitation.

There are presently ultrasonic systems in existence whose frame rates are in the vicinity of 10 to 20 frames per second. These are limited in their usefulness for the reasons stated above, and an attempt to reduce the apparent flicker by using longer persistence screens only serves to further reduce the resolution of the image of a moving target by smearing this image on the oscilloscope screen. Even at 60 frames per second, the valvular motion of the heart distorts the linearity of the image on the screen since the peak velocities of the heart valve leaflets may be as high as 120 millimeters per second. The normal range is in the vicinity of 60 to 80 millimeters per second, and stenotic valves may move 5 to 10 millimeters per second. At this high velocity, the valve leaflet would move 1.66 millimeters per frame, whereas at a frame rate of 15, the valve would move 6.66 millimeters per frame, which can seriously distort the valve image, if indeed it can be seen at all under these circumstances.

The optimum frequency for the transducer for examining the adult human heart is approximately 2.25 megahertz. This considers the acoustic absorption as a function of depth and the beam shape. A focused transducer offers some advantages over nonfocused systems, and inasmuch as the valvular structures of the heart lie approximately 10 centimeters below the skin surface, a 10 centimeter focal length is selected for most adult patients. A frequency of 3.5 MHZ is considered the best choice for pediatric examinations, with a 5 centimeter focal length. A 0.5 (12.7 mm) inch diameter transducer can be utilized for examining the heart through the intercostal spaces. The wave length of sound at 2.25 MHZ is 0.66 millimeters, and thus the transducer is approximately 19 wave lengths in diameter. This is sufficient for weak focusing capability at depths of 10 centimeters, thus a beam width of 4 millimeters at the half power point can be achieved, and lateral resolution of 2 millimeters can be achieved for strong echoes. The range resolution is a function of pulse length. A pulse of 1 and ½ acoustic cycles can readily be achieved by state of the art techniques; therefore, 1 millimeter longitudinal resolution is attainable with this device.

The presently disclosed apparatus permits the use of either B-mode or M-mode, or simultaneous B-mode and M-mode operation. The information from the sector scan of the B-mode may be used by the physician to modulate the M-mode data. This combined M-mode and B-mode display contains more information than the standard M-mode, and it is possible for the physician to learn to interpret the new information and format contained in the combined display. It has been the custom of many cardiologists to angularly sweep the transducer gradually over the heart from base to apex during an M-mode examination of the heart, directing the transducer to the various features of the heart of interest during the course of the scan in order to visualize the valves and structures important to the diagnosis; thus, the surface described by the sweep is a nonplanar complex surface and requires knowledge and skill by the operator.

It is easier to include the various valves and other structures in the scan when the simultaneous B-mode and M-mode sweep (from base to apex) is used, with a B-mode sweep at right angles to the slow manual sweep. With the B-mode shut off, the physician has the same equipment which he customarily uses for M-mode operation, and therefore there is no compromise to the quality of the operator's M-mode examination. The operator may also use the B-mode without the M-mode display in operation, and diagnostic criteria will be established for B-mode alone. The most promising technique, however, appears to be combined M-mode and B-mode capability. There are features of combined mode of operation which cannot readily be duplicated by the single mode operation, and this combined system has been designed to provide both modes with no compromise in design features for either the M- or B-mode of operation.

The B-mode operation is used to best advantage if the operator can record the dynamic pictures appearing on the oscilloscope screen. Both motion picture film and TV recording techniques can be adapted to the present system. It is not only important to be able to replay the real time display, but also to examine single frames in detail. Both the movie and TV approaches permit this freedom. Particularly with stop frame examination, it is important to know what part of the cardiac cycle is represented in the frame. It has been customary to display the ECG date for this purpose; however, in the present system, a digital clock is utilized to show seconds, tenths of second and hundreths of seconds, and the clock is reset to 0 following each R-wave. The digital readout is placed adjacent to the B-mode display, thus permitting the physician to accurately determine the stage of the cardiac cycle being viewed in stop frame operation. Other alpha numeric data can also be recorded, by placing the readout within the field of view of the camera, such as patient number, record number, date, etc.

The present ultrasonic probe apparatus shall now be described in detail in conjunction with the accompanying figures in which.

Figure 1:
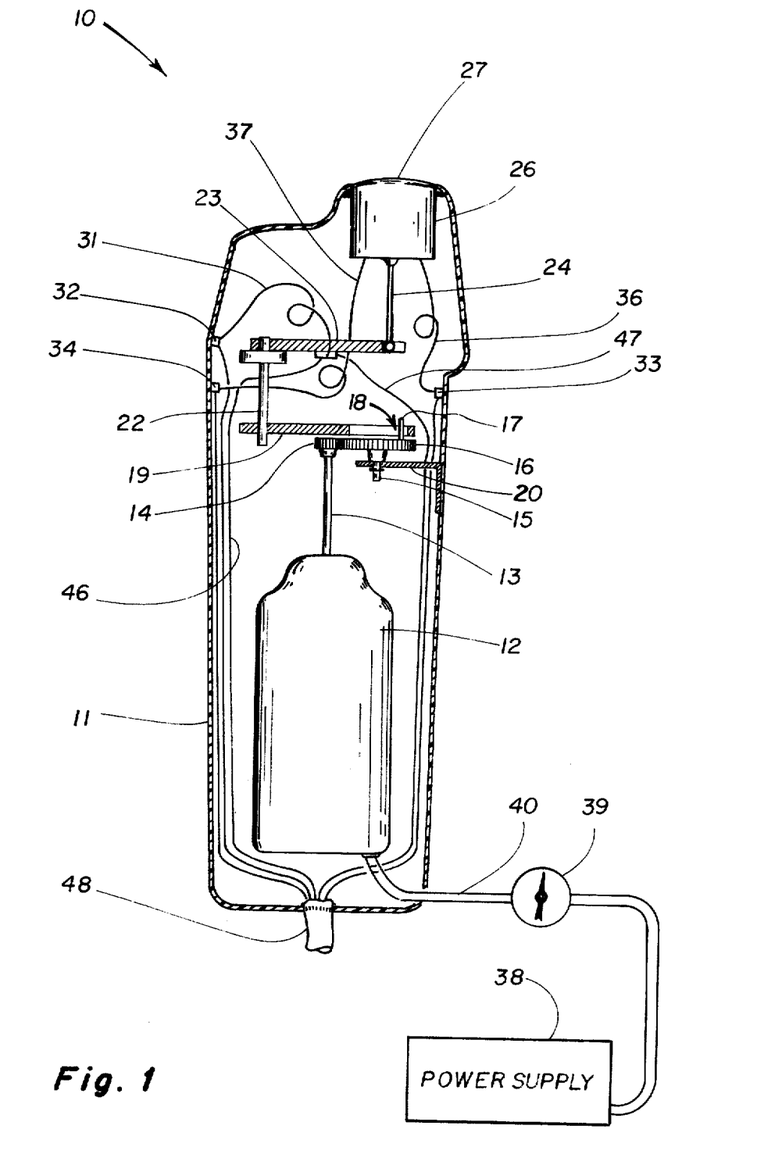
FIG. 1 is a partially diagrammatic, partially cross-sectional, side view of an ultrasonic probe according to an embodiment of the present invention.

Referring in particular to FIG. 1, there is shown an ultrasonic probe 10 having a casing 11 and motor 12 mounted therein. Housing 11 is a plastic shell in order to minimize shock hazards to a patient and the operator. The shell is in the form of a tapered cylinder and provides a compartment for motor 12, which operates at a low voltage, also to minimize shock hazard. In order to obtain good torque characteristics, the motor operates at high speeds and is geared down to usable output shaft speed with spur gear sequence. Motor 12 drives shaft 13 which terminates in gear 14. Gear 14 engages gear 16, which includes eccentric pin 17 attached rigidly to its upper surface. Gear 16 is mounted on output shaft 15; shaft 15 is rotatably mounted on a plate 20 attached to housing 11, and gear 16 held in position between the plate 20 and arm 19.

As gear 16 rotates, eccentric pin 17 drives arm 19, rigidly attached to shaft 22, and arm 23, which is also rigidly attached to shaft 22, through an angle of 30°, sweeping through this arc twice per revolution of the output shaft 15. When arm 23 is driven through the arc of 30°, lever 24, rigidly attached to the transducer housing 26 at a first end, engages arm 23 in a ball-and-socket arrangement at its second end and rotates transducer 27 through a 30° arc. The bottom of lever 24 freely pivots in the socket in the upper end portion of arm 23 as shown in FIG. 1. Transducer face 27 is thereby oscillated about an axis which lies in a plane perpendicular to the long dimension of probe 10.

Figure 2:
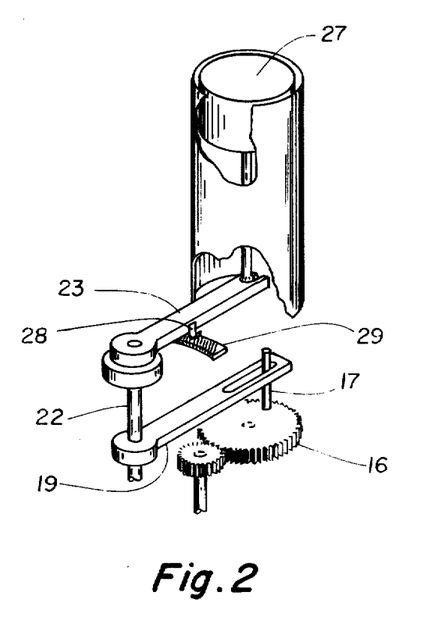
FIG. 2 is a perspective view of the transducer end portion of the probe of FIG. 1.

As shown most clearly in FIG. 2, an electrical wiper contact 28 is attached to arm 23. Wiper contact 28 engages position-sensing pot 29, and an electrical lead 31 (FIG. 1) from the wiper contact passes along the top of the arm past the axis of rotation and terminates on a binding post 32. The looped configuration of this wire is important from the point of view of minimizing breakage due to flexing. The electrical connections between the oscillating transducer 26 and the stationary binding post 33 and 34 must also be properly designed in order to minimize failure due to flexing. Transducer wires 36 and 37 are attached between transducer 26 and binding post 33 and 34, respectively.

The factors included in the electrical connection design include the use of tensile conductors wrapped around a cotton core and covered with a flexible plastic sheath, such as polyurethane insulation. Flexing per unit length of wire is minimized by using a loop of wire in the plane of flex, and to avoid a concentration of stress at the terminals a tapered silastic covering is applied over the wires to give a gradual transition in stiffness from the rigid binding posts to the very flexible lead wires. The wires are carefully positioned so that they will not contact other objects in the course of their rotation or other movement.

An electrical switch may be provided on the housing to enable the operator to start and stop motor 12. If the operator wishes to stop the transducer so that it is aimed along the axis of probe 10, the speed control 39 for motor 12 is turned to a very low speed operation, and when the transducer has the proper orientation, the power switch is turned off. This may be done if the equipment is to be used in the M-mode only. As shown in FIG. 1, power supply 38, operating through speed control 39, is supplied to energize motor 12. The operator-controlled on-off switch may be easily located at the tapered portion near the head of housing 11 for easy control by extending power supply wires 40 into the housing to run past the switch location.

Figure 3:
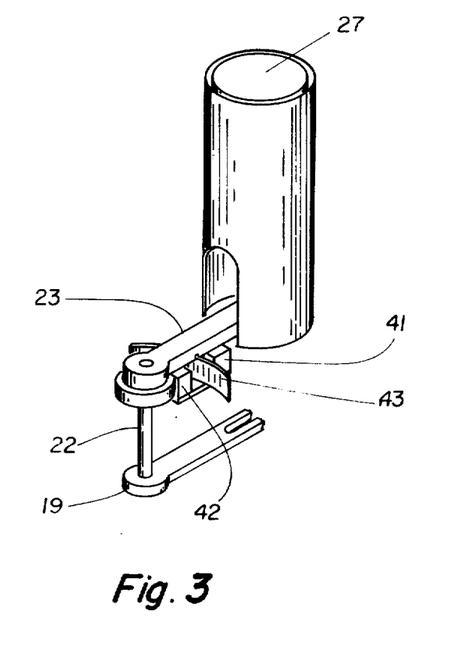
FIG. 3 is a perspective view similar to FIG. 2 showing a light source and optical wedge apparatus instead of the resistance pad of FIG. 2.

As shown in FIG. 3, the probe may be modified to include source light 41 and light receiver 42 rigidly attached to housing 11 beneath moving arm 23. Optical wedge 43 is then mounted to moving arm 23 and passes between light source 41 and light receiver 42. With wedge 43 attached to arm 23 moving through the arc scanned and the photo receiver and source opposite one another on either side of the wedge, the light passing from the photo source to the photo receiver is modulated by the variable density filter, the optical wedge, moving past it. The resultant electrical signal is taken from the optical receiver and amplified, and used as an input for X sweep generating circuits of the viewer.

The resistance system of FIG. 2 includes a wiper mounted on the arm that is moving through the scanned arc and a special resistance pad rigidly attached to housing 11. The pad must be of a very hard and smooth material with a low coefficient of friction, long life, and low noise properties such as a plastic element. A voltage is applied across the resistance strip and the wiper takes off a voltage from it that is a function of the angle at which the arm is positioned. The position-sensing element can be of other varieties besides resistive and optical such as magnetic or inductive.

In normal operation, for examination of the heart, the transducer 26 is placed in contact with the skin with a suitable coupling material. Most adults tolerate the oscillatory motion of the transducer and experience no discomfort. In using the device for pediatrics, scanning young children and infants, the vibration produced by the transducer may be alarming in a few cases to the subject. To avoid this problem a small water capsule 2 inches in diameter and ½ inch thick is placed on the child's chest using a suitable coupling agent, and the transducer is then placed over the capsule. The vibration of the transducer is completely shielded by this method and avoids any squirming response of the patient.

Figure 4:
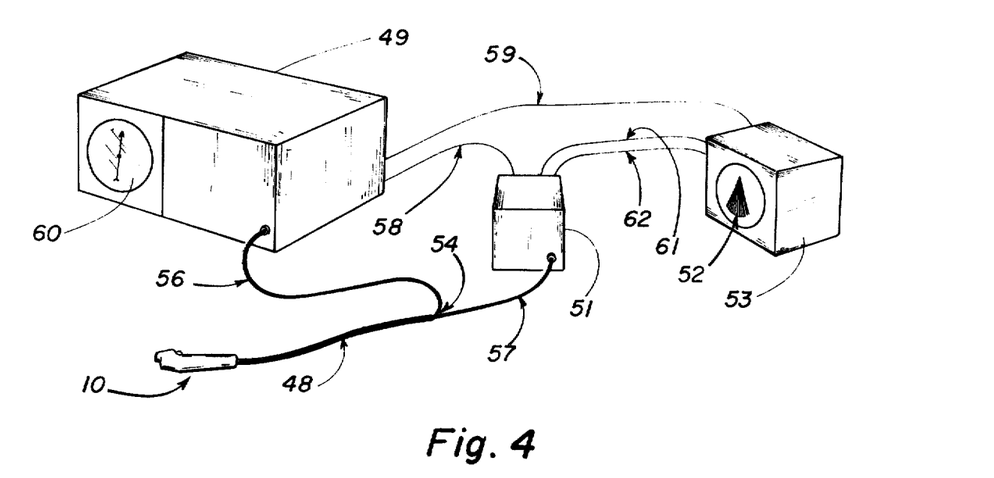
FIG. 4 is a diagrammatic view of an ultrasonic scan system according to an embodiment of the present invention.

Wires 46 and 47 are connected from opposite ends of resistance pad 29 (FIG. 1), and these wires together with wires 31, 36 and 37 are gathered together mechanically within housing 11 and coupled to cable 48 by suitable connector means. As shown in FIG. 4, the wires in cable 48 are coupled through a T connector to a modified M-mode display unit 49, such as an Ekoline 20 manufactured by the Smith Kline Instrument Company of Palo Alto, California. Cable 48 is also coupled to Y-axis generator circuit 51. The display system uses a medium persistance oscilloscope to display the real time acoustic image. The display raster is an arc sector 52 generated by a vertical sweep sawtooth signal of the same period as the PRF clock in unit 49, and a variable slope horizontal sawtooth wave form of the same period as the PRF clock. Conventional CRT sawtooth units are provided with rectangular coordinate display format which must be transformed to polar coordinates to display a sector raster. Due to the small angles involved, X-axis correction is not necessary. The vertical Y sweep for the B-mode display is modulated by the cosine of the angle that the transducer is rotated through, and the horizontal X sweep should theoretically be modulated by the sine of the angle. For the 30° scan angle utilized, it has been found that X-axis correction is not necessary due to the small error introduced. This produces a resultant vector that is essentially geometrically correct. These functions are derived from the position-sensing elements on the ultrasonic probe. The position sensing element may be optical, resistive and so on as discussed above in regard to FIGS. 2 and 3.

Display unit 49, such as an Ekoline 20, is modified in the present system as to the various necessary internal time constants to permit operation at a 5,000 PRF rather than 1,000, for which the unit is designed. The additional sweep circuitry of unit 51 is provided to drive CRT 53 and a sweep circuit modification similar to the circuitry in unit 51 is provided for the Ekoline 20 unit 49, as described below in more detail.

As shown in FIG. 4, the various wires from the transducer, potentiometer and motor and travel within cable 48 to point 54 where coaxial cable 56 couples the transducer wires to unit 49 and the remaining wires are coupled by cable 57 to module 51. Cable 58 couples a PRF pulse from unit 49 to module 51, and cable 59 couples the Z, or intensity, signal from unit 49 to oscilloscope 53. Cables 61 and 62 couple the horizontal and vertical sweep outputs from module 51 to oscilloscope 53. In B-mode operation of probe 10, a B-mode display is obtained on the screen of oscilloscope 53 through the coordination of M-mode unit 49 and B-mode module 51. For M-mode display only, the transducer in probe 10 is maintained in a nonoscillatory condition and only the M-mode display is produced by the coupling of the transducer through cables 48 and 56 to the M-mode unit 49. The "ice pick" M-mode display appears on screen 60 of M-mode unit 49, and module 51 is turned off as is oscilloscope 53. The M-mode display unit 49, preferably an Ekoline 20 unit, is primarily modified simply as to its time constants to process the transducer signal at a PRF of 5,000 rather than 1,000, at which frequency the Ekoline 20 is normally operated.

Figure 5:
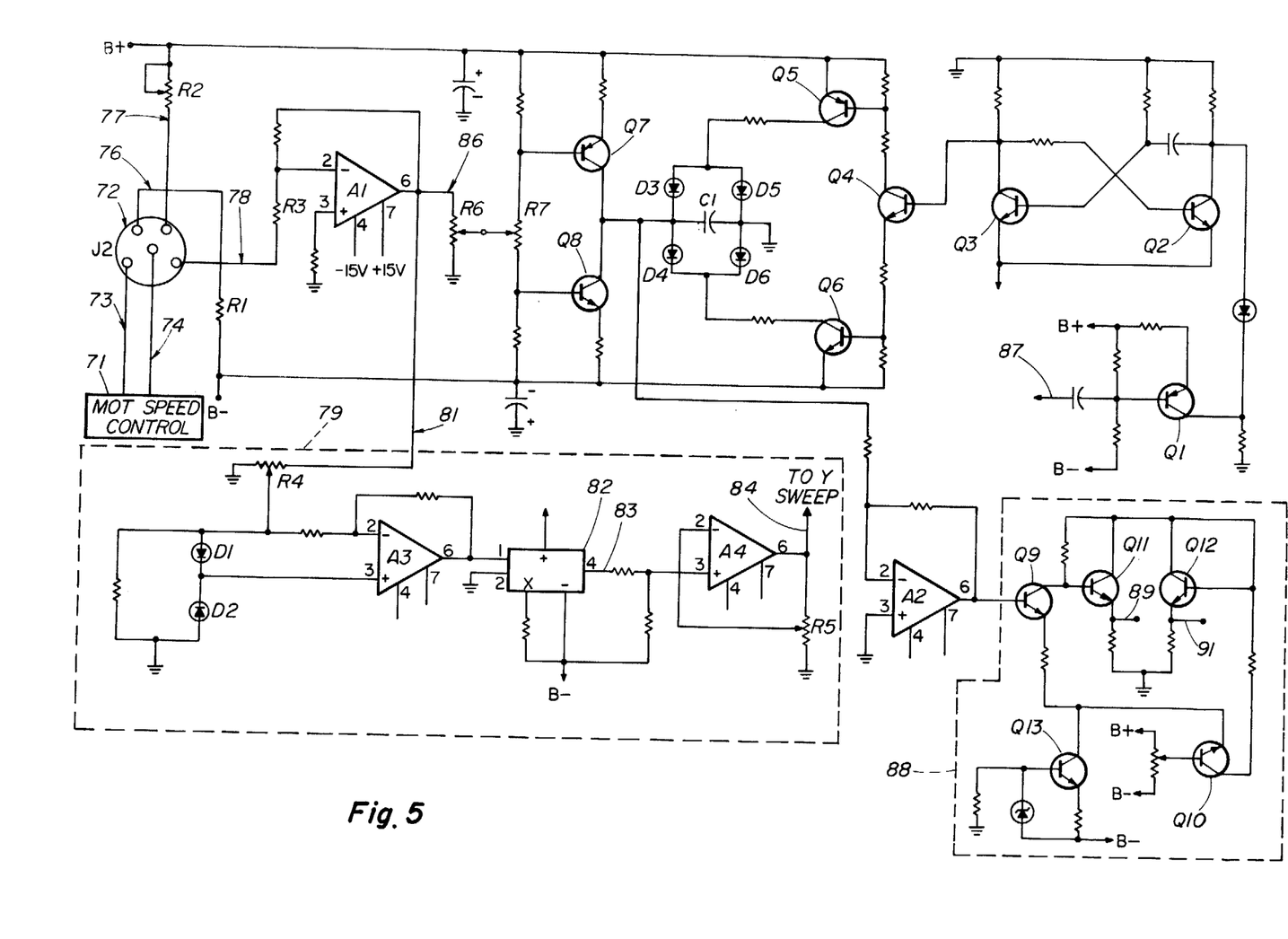
FIG. 5 is a schematic view of a portion of the sweep circuitry according to an embodiment of the present invention.

Turning now to FIG. 5, there is shown circuitry for X-axis sweep generation for B-mode display and cosine correction generation and a block diagram indication of the motor speed control contained in sweep generator unit 51. Motor speed control 71 provides an on-off switch and variable voltage speed control for the motor in probe 10 (FIG. 4). The two motor wires from cables 48 and 57 are coupled through connector 72 in the face of module 51 and coupled to the motor speed control through leads 73 and 74.

The left end of the resistive element in probe 10 is coupled through connector 72, lead 76 and resistor R1 to a negative supply voltage. The right side of the resistive element in the probe is coupled through connector 72, lead 77 and variable resistor R2 to a positive DC supply. This establishes a voltage divider from the B+ through R2, the resistive element in the probe, and R1 to B−. The wiper arm from the probe is coupled through the connector and lead 78 and resistor R3 to operational amplifier A1. Amplifier A1 and the other amplifiers in the circuit have the usual plus and minus 15 volt connections, etc. The wiper arm input voltage to A1 is a function of the position of the transducer as it oscillates on its axis. This signal is similar to a sinusodal wave form and is a function of the angular position of the transducer.

The amplified signal from the output of A1 is coupled to cosine generator circuit section 79 through conductor 81. The wiper arm of potentiometer R4 picks off a portion of the signal from the output of A1, and a full wave rectifying circuit including A3, D1 and D2 generates the absolute value of the signal. This full wave rectified signal is fed into function generator 82, e.g. a Burr Brown Sin Cos Function Generator 4118/25, which produces at its output 83 a signal which is the cosine of the input voltage. This signal is now a function of the cosine of the angular position of the transducer in probe 10. The output cosine signal from function generator 82 is amplified by amplifier A4 and fed to potentiometer R5. The output 84 of the cosine generator circuit section 79 is supplied to the Y sweep generator circuitry in unit 51 for B-mode display and modulates the Y-axis sweep signal, as shall be explained in further detail hereinafter.

The Y-axis sweep is modulated, as described above, by the cosine of the angle that the transducer is swept through to produce the correct vectorial vertical component of deflection on the oscilloscope screen for B-mode scanning. The cosine function is derived from the position sensing signal, as described above, and since the position sensing signal goes above and below the ground potential as the transducer swings from right through center to left, a full wave rectifier is used to make the signal positive in both quadrants, since the cosine is positive for these quadrants. The output of the sine cosine module is then a voltage proportional to the cosine of the angle of the transducer, which is a voltage proportional to the position signal from the wiper arm of the potentiometer in the probe 10.

The transducer angle-dependent wave form at the output of A1 is also coupled for X-axis sweep generation through lead 86 to potentiometer R6, the wiper arm of which picks off a portion of the amplitude of the wave form. Coupled to the wiper arm of R6 is a wiper arm of potentiometer R7 which determines the bias of the wave form, serving as a voltage divider between B+ and B−. The amplified position-sensing signal from the probe transducer is then input to a complimentary current source comprising transistors Q7 and Q8. The signal appears as a variable voltage on the collectors of Q7 and Q8, and capacitor C1 then charges up to this voltage. The slope of the voltage ramp that is created on capacitor C1 is a function of the instantaneous input signal amplitude on the collectors of Q7 and Q8. The ramp voltage thus produced on C1 would continue to rise up to the supply voltage if retrace did not occur.

Retrace is accomplished by diodes D3, D4, D5 and D6 and transistors Q5 and Q6. The initiation of the retrace period occurs in the circuitry at the right-hand side of FIG. 5 with a pulse input through lead 58 (FIG. 4) from unit 49 to module 51 at the point labeled 87 in FIG. 5. The PRF pulse coupled from unit 49 is a positive pulse of about 15 microsecond duration and 2 volts in height and is derived from the PRF clock in Ekoline 20, unit 49. An amplifier stage comprising transistor Q1 inverts and amplifies the input pulse and feeds it to one shot multivibrator comprising Q2 and Q3. The narrow pulse from the one shot multivibrator is fed to the base of transistor Q4, which uses the pulse to turn on Q5 and Q6. As current in Q5 and Q6 increases, diodes D3, D4, D5 and D6 conduct and capacitor C1 is discharged, thus returning the ramp voltage on C1 to 0. Therefore, a variable slope ramp signal is produced at PRF repetition rate with C1 charging toward the instantaneous voltage at the collectors of Q7 and Q8.

The variable slope ramp generator signal from capacitor C1 is then preamplified by amplifier A2 and input into the differential output amplilfier section 88. The differential amplifier comprises transistors Q9 and Q10 and constant current source Q13 which provides linearity and high frequency response at the gains necessary to deflect the plates of the CRT 53. Emitter follower transistors Q11 and Q12 provide a low impedance driver for the plates of the CRT. The output to the horizontal deflection plates of CRT 53 are shown at 89 and 91.

Figure 6:
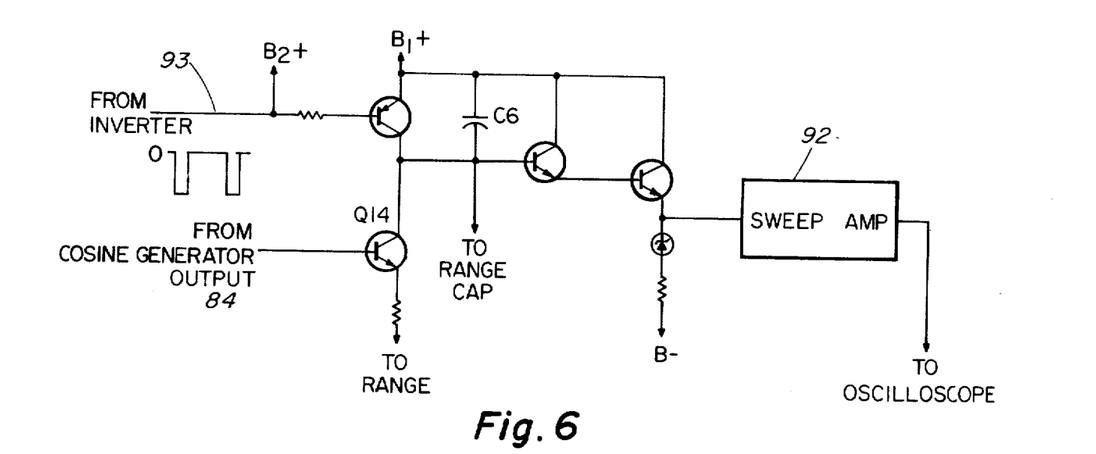
FIG. 6 is a schematic view of a sweep generator circuit for the embodiment of FIG. 5.

Referring now to FIG. 6, there is shown a Y-axis sweep generator circuit, also included in module 51, whose output is coupled to sweep amplifier 92, which is of the same configuration as sweep amplifier circuit section 88 in FIG. 5. This sweep amplifier circuitry 92 is contained in module 51 and provides the Y-axis sweep to oscilloscope 53. Negative pulses at the PRF rate are provided from the inverter circuit in the Y-axis, or fast axis, sweep section of the M-mode display unit 49, the Ekoline 20. The sweep circuitry shown is essentially the same as that used in the M-mode display unit 49, with C6 producing effectively a sawtooth wave which is amplified by sweep amplifier 92 to provide the Y-axis or vertical deflection for oscilloscope 53. Transistor Q14 is inserted in series with the usual range control for the sweep circuit and has an input at its base from the output 84 of the cosine generator section 79 of the circuit of FIG. 5. This cosine generator output 84 being applied to the base of Q14 provides a modulation of the vertical deflection sawtooth slope so that the correct amount of vertical deflection is provided in accordance with the angle of the sweep in the B-mode display.

As shown in FIG. 6, the cosine wave generated in subcircuit 79 is fed to the base of transistor Q14 and modulates the slope of the sawtooth produced at C6 in the sweep generator circuit. The effect of this additional modulation is to produce a Y-axis sweep sawtooth whose slope varies slightly according to the cosine of the angular position of the transducer and of the scanned line. As indicated above, this sawtooth is fed to the sweep amplifier which then couples the amplified sawtooth to the plates of oscilloscope 53 for vertical deflection. A sweep amplifier section such as 92 or 88 is also substituted for the original sweep amplifier section for the fast scan, or Y, axis of the M-mode display unit 49 in order to facilitate operation at a PRF of 5,000.

The remaining scanning function of the M-mode display unit 49 is not effected by the modifications described above. This X-axis scan of the M-mode display is of slow speed and not correlated to the PRF.

Therefore, modifications to the sweep circuitry for the slow scan deflection of the M-mode display is not necessary. It can be seen that a B-mode ultrasonic scan display system has been described which may readily be retrofit with an existing M-mode system and which provide fast-scan real-time viewing of the interior of structure such as the human heart.

While there have been described above the principles of this invention in conneciton with specific apparatus, it is to be clearly understood that this description is made only by way of example and not as a limitation in the scope of the invention.

What is claimed is:

1. Ultrasonic probe apparatus comprising:
   an elongated probe housing having a longest dimension;
   a transducer pivotally mounted near an end of the housing and having a face adjacent the surface of the housing, the transducer being pivoted about an axis in a plane approximately perpendicular to the longest dimension of the housing;
   linkage means in the housing for pivotally oscillating the transducer about its axis when the linkage means is activated;
   motor means coupled to the linkage means for activating the linkage means; and
   means coupled to the transducer for causing the transducer to produce ultrasonic pulses.

2. The apparatus of claim 1 which further comprises indicator means mounted within the housing for indicating the angular position of the transducer as it is pivotally oscillated by the linkage means.

3. The apparatus of claim 2 in which the linkage means includes a first wheel having an eccentric pin extending from its first surface, a slotted lever positioned with the eccentric pin within the slot in the slotted lever, and an arm rigidly attached to the transducer at a first end and having a second end pivotally coupled to the slotted lever, whereby rotation of the wheel and consequent oscillation of the slotted lever is translated into oscillatory motion of the arm and transducer.

4. The apparatus of claim 3 in which the linkage means further comprise a first shaft rigidly attached at the end of the slotted lever further from the slot and positioned essentially parallel to the pin, a second lever rigidly attached to the first shaft and essentially parallel to the slotted shaft in spaced apart relationship from the slotted shaft, the second level including a socket pivotally receiving the arm of the transducer.

5. The apparatus of claim 4 in which the motor is mounted within the housing and includes a motor shaft and a toothed gear rigidly attached to the end of the shaft and the first wheel includes teeth engaged and driven by the teeth in the gear attached to the motor shaft.

6. The apparatus of claim 5 in which the transducer is pivotally mounted to the housing adjacent the face of the transducer.

7. The apparatus of claim 6 in which the indicator means includes a resistance pad coupled to the housing and the second lever includes a contact wiper which moves along the resistance pad as the second lever and transducer are oscillated.

8. The apparatus of claim 1 which further comprises means coupled from the transducer for receiving and for displaying echoes of said ultrasonic pulses.

9. The apparatus of claim 1 in which the motor means includes a variable speed control for varying the speed of the motor and consequently varying the frequency of oscillation of the transducer.

* * * * *

UNITED STATES PATENT OFFICE
CERTIFICATE OF CORRECTION

Patent No. 3,955,561         Dated May 11, 1976

Inventor(s) Reginald C. Eggleton

It is certified that error appears in the above-identified patent and that said Letters Patent are hereby corrected as shown below:

Col. 3, Line 61 "date" should be --data--

Col. 6, Line 9 "sawtooth" should be --display--

Col. 10, Line 13 "level" should be --lever--

Signed and Sealed this

Seventh Day of September 1976

[SEAL]

Attest:

RUTH C. MASON
Attesting Officer

C. MARSHALL DANN
Commissioner of Patents and Trademarks